(12) United States Patent
Rautee et al.

(10) Patent No.: US 7,231,246 B2
(45) Date of Patent: Jun. 12, 2007

(54) DETECTION OF ENCEPHALOPATHY (75) Inventors: Riina Anniina Rautee, Espoo (FI); Mika Särkelä, Helsinki (FI)

(73) Assignee: GE Healthcare Finland Oy, Helsinki (FI)

( * ) Notice: Subject to any disclaimer, the term of this patent is extended or adjusted under 35 U.S.C. 154(b) by 463 days.

(21) Appl. No.: 10/886,485

(22) Filed: Jul. 7, 2004

(65) Prior Publication Data

US 2006/0009709 A1 Jan. 12, 2006

(51) Int. Cl.
*A61B 5/00* (2006.01)
(52) U.S. Cl. ..................... 600/544; 600/545
(58) Field of Classification Search ............. None
See application file for complete search history.

(56) References Cited

U.S. PATENT DOCUMENTS 5,857,979 A * 1/1999 Ryu et al. ............... 600/544
6,731,975 B1 * 5/2004 Viertio-Oja et al. ........ 600/544

FOREIGN PATENT DOCUMENTS

WO WO-02/32305 4/2002

OTHER PUBLICATIONS al Naqeeb et al. "Assessment of Neonatal Encephalopathy by Amplitude-integrated Electroencephalography". 1999; 103:1263-1271. Accessed at http://www.pedatrics.org/cgi/content/full/103/6/1263.*
*Objective Measurement of Hepatic Encephalopathy by means of Automated EEG Analysis*, Carin et al., Electroencaphalography and clinical Neurophysiology, 1984, 47: 423-426.
*Prognosis Significance of EEG Triphasic Waves in Patients with Altered State of Consciousness*, Bahamon-Dussan et al., Journal of Clinical Neurophysiology 6(4):313-319, 1984.
*The EEG in systemic disorders: the encephalopathies*, MacGillivray, Clinical Neurophysiology, vol. 2, EEG, Paediatric Neurophysiology, Special Techniques and Applications, 2003, pp. 308-354.
EP Search Report dated Oct. 24, 2005.
*The EEG Signal in Hepatic Encephalopathy: from a Time-Domain Statistical Analysis Towards Fractional Brownian Processes*, D. Pascoli et al., Fractuals in Biology and Medicine, vol. 3, 2002, pp. 137-146, XP008053424.
*Nonlinear EEG Changes in Postanoxic Encephalopathy*, Cornelis J. Stam, et al., Theory Biosci. (1999) 118: 209-218.
*Comparison of Human Ictal ,Interictal and Normal Non-linear Component Analyses*, Honghui Jin et al., Clinical Neurophysiology 111 (2000) 1282-1292.

* cited by examiner

*Primary Examiner*—Max F. Hindenburg
*Assistant Examiner*—Patricia Mallari
(74) *Attorney, Agent, or Firm*—Andrus, Sceales, Starke & Sawall, LLP (57) ABSTRACT

The invention relates to detection of encephalopathy based on EEG signal data obtained from a patient. A first signal component is derived from the EEG signal data, the first signal component representing low frequencies of the EEG signal data. A first parameter indicative of disorder in the first signal component and a second parameter indicative of disorder in EEG signal data representing a first frequency band are then computed, wherein the first frequency band includes higher frequencies than said low frequencies. An indicator of encephalopathy is then determined based on the first parameter and the second parameter, the indicator of encephalopathy being indicative of encephalopathy.

42 Claims, 4 Drawing Sheets

DETECTION OF ENCEPHALOPATHY

FIELD OF THE INVENTION

The present invention relates generally to detection of cases of encephalopathy. In this context, encephalopathy refers to any disorder of the brain that may be caused by a disease, an injury, drugs, or chemicals. The invention is primarily intended for detecting encephalopathy in intensive care units (ICU), although it may be utilized in various medical environments.

BACKGROUND OF THE INVENTION

Electroencephalography (EEG) is a well-established method for assessing brain activity by recording and analyzing the weak biopotential signals generated in the cortex of the brain with electrodes attached on the skin of the skull surface. The EEG has been in wide use for decades in basic research of the neural systems of the brain, as well as in clinical diagnosis of various neurophysiological diseases and disorders. Since the present invention is based on an EEG signal, the EEG signal and its appearances in systemic disorders are discussed first.

The EEG signal represents the sum of excitatory and inhibitory potentials of large numbers of cortical pyramidal neurons, which are organized in columns. Each EEG electrode senses the average activity of several thousands of cortical pyramidal neurons.

The EEG signal is often divided into four different frequency bands: Delta (0.5–3.5 Hz), Theta (3.5–7.0 Hz), Alpha (7.0–13.0 Hz), and Beta (13.0–32.0 Hz). Alpha waves are found during periods of wakefulness, and they may disappear entirely during sleep. Beta waves are recorded during periods of intense activation of the central nervous system. The lower frequency Theta and Delta waves reflect drowsiness and periods of deep sleep.

Different derangements of internal system homeostasis disturb the environment in which the brain operates, and therefore the function of the brain and the resulting EEG are disturbed. The EEG signal is a very sensitive measure of these neuronal derangements, which might be reflected in the EEG signal either as changes in membrane potentials or as changes in synaptic transmission. A change in synaptic transmission occurs whenever there is an imbalance between consumption and supply of energy in the brain. This means that the EEG signal serves as an early warning of a developing injury in the brain.

Diagnostically, the EEG is not specific, since many systemic disorders of the brain produce similar EEG manifestations. In the ICUs, an EEG signal may be of critical value, as it may differentiate between broad categories of psychogenic, epileptic, metabolic-toxic, encephalitic and focal conditions. However, in many of these conditions, the EEG signal is incidental and hardly critical to the diagnosis or clinical management. However, the EEG signal may be used to detect intracranial changes earlier than by conventional methods. According to the present state of knowledge, the EEG signal is regarded as an effective tool for monitoring changes in the cerebral state of a patient.

In ICU surroundings, the EEG signal is quite often measured by using two channels: C3-P3 and C4-P4. In this way, localized abnormalities are overlooked, but the measurement is easier to carry on, since the number of electrodes is small. Long-term monitoring of the EEG is not yet common in ICU surroundings, and so far the emphasis has been on diagnostic applications using the raw EEG signal.

Encephalopathy commonly refers to metabolic and systemic disorders of the brain, which are secondary to and/or consequent upon systemic diseases or conditions. Encephalopathies are not cerebral in origin.

Recent studies of non-sedated, critically ill patients suggest that up to 70 per cent of such patients have clinical evidence of altered consciousness consistent with encephalopathy. The precise effect of critical illness encephalopathy, i.e. a distinct form of encephalopathy, is not known, as there is no agreed way of diagnosing it.

Most of the metabolic and systemic disorders have EEG correlates, and if there is a disturbance of conscious level, the EEG is never normal. However, the EEG findings in encephalopathy have many similarities to those during sedation and anesthesia, which makes the detection of encephalopathy in sedated patients difficult. Generally, when a patient loses consciousness, a shift of spectral power towards lower frequencies appears. In a sedated but healthy brain, sedation induces more order in the EEG signal. Sedation is often said to resemble natural sleep, even though counter arguing opinions exist. An EEG signal measured during sleep is said to have a structural polyphasic pattern. This pattern should be quite different from the one seen in most metabolic disorders, which in its more severe manifestations appears as a monotonic shift towards statistical stationarity.

The difficulty of distinguishing encephalopathy from sedation may be one reason for the EEG being often an underused and a misunderstood clinical resource. Namely, it is often so that as the brain is buffered by the blood-brain barrier, the EEG correlates with clinical behavioural states are better than with peripheral chemistry, such as blood samples. These correlations are enhanced by the objectivity of quantitative EEG (qEEG) measures, even though no consensus of the appropriate methodology of qEEG measurements exists at the moment. A lack of international recommendations has decelerated the advances in commercially available algorithms and monitoring platforms. Below, different uses of the EEG in an ICU are discussed.

Briefly, the EEG signal has a limited repertoire of responses in most of the systemic metabolic disorders, which may be of help when detecting encephalopathies. However, none of the responses is in any way specific to particular conditions. The following describes the repertoire of EEG responses during encephalopathy:

slowing of the dominant alpha rhythm, where a frequency of 7.5 Hz can be taken as abnormal;

an increase in Theta frequencies;

often paroxysmal Delta activity;

triphasic waves;

fallout of all faster frequencies and a falling amplitude (terminal patients); and isoelectricity (terminal patients).

The monitoring and detection of the above conditions is based on the clinician's subjective analysis of the raw EEG signal. In the following, the current monitoring methods of some encephalopathy types are discussed briefly.

In status epilepticus the epileptic spikes typically last only for a fraction of seconds, but the use of the EEG leans towards the fact that by using long lasting recordings, the EEG signal can reflect slow trend changes. Also, if a seizure occurs during measurements, the EEG signal may categorize the epileptiform patterns and seizure activity as a specific type of epilepsy, as well as identify the non-convulsive forms of status epilepticus. In addition, the EEG signal may be used as a control tool for inducing a barbiturate sleep to a level where there are no visible seizures. In this kind of monitoring, an EEG signal from several channels is needed.

In coma, which is the far end of a metabolic encephalopathy, or if brain death is suspected, EEG correlates with the grade of neuronal dysfunction (severity of brain injury) and therefore gives a prognosis for the recovery of the patient. In this sense, the clinician again interprets the raw EEG. A good sign concerning the patient's recovery is the reactivity of the EEG signal. On the other end, in a deeper coma, the isoelectricity of EEG suggests brain death. Despite this important indication, the isoelectricity of the EEG signal does not alone confirm the brain death; other methods like angiography are used as well to ensure the diagnosis.

Global cerebral hypoxia and ischemia belong to the commonest of all clinical disorders of the brain, and they result from local or generalized hypoxic-ischemic events. The patterns of the EEG signal include, for example, generalized suppression (isoelectric EEG), which after a day of recording indicates either permanent vegetative state or death, and burst suppression, which in turn predicts a poor outcome after a head trauma, for example. Although being categorized as a primary brain injury, generalized cerebral hypoxia is also a true metabolic disorder, and can be categorized as encephalopathy.

Generally, if a patient is unconscious (without sedation), the reason in 30 to 40 per cent of the cases is intracranial, whereas in 60 to 70 per cent of the cases unconsciousness is due to hypoxic-ischaemic, metabolic, or toxic reasons. This kind of general unconsciousness is currently monitored with the help of the Glasgow Coma Scale. It defines the patient (un)consciousness by using three parameters: eye opening, best motoric response, and best response to speech. Table 1 below illustrates the Glasgow Coma Scale. As can be seen, this method is subjective and inter-rater variability may be large.

TABLE 1

The Glasgow Coma Scale

| Criterion | | Points |
|---|---|---|
| Eye Opening Response | Spontaneous | 4 |
| | Opens to verbal command | 3 |
| | Opens to pain | 2 |
| | None | 1 |
| Verbal response | Oriented | 5 |
| | Confused | 4 |
| | Inappropriate words | 3 |
| | Incomprehensible sounds | 2 |
| | None | 1 |
| Motor response | Obeys commands | 6 |
| | Localises pain | 5 |
| | Withdraws from pain | 4 |
| | Abnormal flexion | 3 |
| | Extends to pain | 2 |
| | None | 1 |
| Total | | 3–15 |

Virtually every patient being cared for in an ICU receives some form of sedation. However, the control of the depth of the sedation administered to a patient is still problematic, and therefore oversedation and undersedation are both common occurrences in ICUs. Although sedation assessment is currently evolving towards a more disciplined and standard part of clinical practice, in which different objective sedation assessment tools are used in order to improve the reliability of the sedation assessment, monitoring the level of sedation is at present mainly handled by using subjective observations from the patient. Various sedation assessment scales have been developed for subjectively assessing the level of sedation, the Ramsay Score being one of the most widely used tool for this purpose. These scoring systems typically assess the different components of the state of the patient, namely motoric and hypnotic components, and the level of agitation.

An objective tool for assessing the level of anesthesia or sedation is disclosed in international patent application WO 02/32305, which depicts a method and device for ascertaining the cerebral state of a patient. In this disclosure, a measure derived from EMG signal data enhances and confirms the determination of the hypnotic state made using EEG signal data. As the EMG data may be computed more frequently than the EEG data, this renders ascertaining changes in the hypnotic state of the patient more rapid. The combined indication provided by the EEG signal data, indicative of the hypnotic component, and EMG signal data, indicative of the motoric component, may also be used for assessing the adequacy of anesthesia or the level of sedation.

However, the new tools for assessing anesthesia and sedation are not able to detect encephalopathy, and no specific parameters for the automatic detection of encephalopathy exist at the moment. Therefore, the detection is at present still based on a clinician's subjective analysis on the state of the patient and the characteristics of the EEG signal. However, the detection of encephalopathy is difficult, since there is often a contradiction between the external appearance and the actual state of the patient, especially in an ICU where the patients are normally sedated. A patient having encephalopathy may appear as being awake in a sort of ailing state. As a result of this, the infusion rates of sedatives may be increased, although the actual state of the patient would not require such an increase. This increases the risk of over-sedation and the problems related to that.

The present invention seeks to eliminate the above-mentioned drawbacks and to bring about a method by means of which encephalopathic patients may be distinguished from patients being sedated but having a healthy brain.

SUMMARY OF THE INVENTION

The present invention seeks to provide a method and arrangement for reliably detecting the abnormality of the brain caused by encephalopathy and for sorting out patients with brain dysfunction from among patients being sedated and but having healthy brains.

The invention is based on the discovery that encephalopathy induces disorder to the low frequency range of the EEG, especially to the Delta waves. The spectral entropy of the low frequency range of the EEG can therefore be used as a categorization tool for discriminating between patients with healthy, sedated brains and patients having encephalopathic (non)-sedated brains.

Thus one aspect of the invention is providing a method for detecting a case of encephalopathy. The method includes the steps of obtaining EEG signal data from a patient and deriving a first signal component from the EEG signal data, wherein the first signal component represents a first frequency band of the EEG signal data, the first frequency band including low frequencies of the EEG signal data. The method further includes computing a first parameter indicative of disorder in the first signal component and a second parameter indicative of disorder in signal data representing a second frequency band of the EEG signal data, the second frequency band including higher frequencies than the first frequency band. The method also includes determining an indicator of encephalopathy based on the first parameter and the second parameter, the indicator of encephalopathy being indicative of encephalopathy.

By means of the invention, patients may be classified into different categories depending on whether encephalopathy is detected or not. Such categories may be, for example, "brain normal but too much medicine" or "unconscious mainly due to encephalopathy". In this way, the titration of sedative drugs can be made more accurate, and drug costs may also be decreased. More accurate titration of sedatives may also decrease the ventilator time required, which may in turn decrease the length of stay of patients in the ICU.

A further advantage of the invention is that current monitoring devices capable of computing the entropy of an EEG signal may easily be modified to detect encephalopathy according to the present invention.

Another aspect of the invention is that of providing an arrangement for detecting a case of encephalopathy. The arrangement includes measurement means for obtaining EEG signal data from a patient and first means for deriving a first signal component from the EEG signal data, wherein the first signal component represents a first frequency band of the EEG signal data, the first frequency band including low frequencies of the EEG signal data. The arrangement further includes computing means for computing a first parameter indicative of disorder in the first signal component and a second parameter indicative of disorder in signal data representing a second frequency band of the EEG signal data, the second frequency band including higher frequencies than the first frequency band. The arrangement also includes determination means for determining an indicator of encephalopathy based on the first parameter and the second parameter, the indicator of encephalopathy being indicative of encephalopathy.

A further aspect of the invention is that of providing a method for assisting a physician. The method includes the above steps of the method for detecting a case of encephalopathy, and an additional step of compiling a treatment recommendation for a physician.

In a still further embodiment, the invention provides a computer program embodied on a computer-readable medium for detecting a case of encephalopathy, the computer program executing the above steps of the method for detecting a case of encephalopathy.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 8 in the appended drawings, wherein.

DETAILED DESCRIPTION OF THE INVENTION

While a patient is deeply sedated and unconscious, the spectral entropy values calculated from the EEG signal are normally low, meaning that the EEG signal consists of regular waves. This has previously been shown by many publications.

As described above, the invention rests on the discovery that encephalopathy induces disorder to the low frequency range of the EEG, i.e. encephalopathy can be seen in the EEG as an increase in the spectral entropy values calculated from the low frequency range of the EEG.

Figure 1:
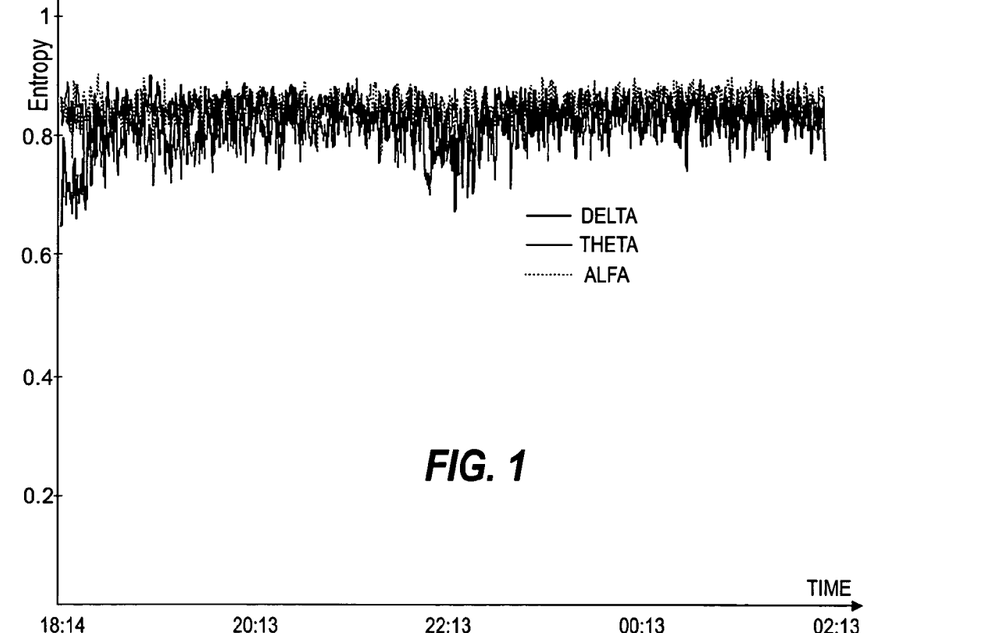
FIG. 1 illustrates the entropies of different EEG rhythms of an encephalopathic patient.
Figure 2:
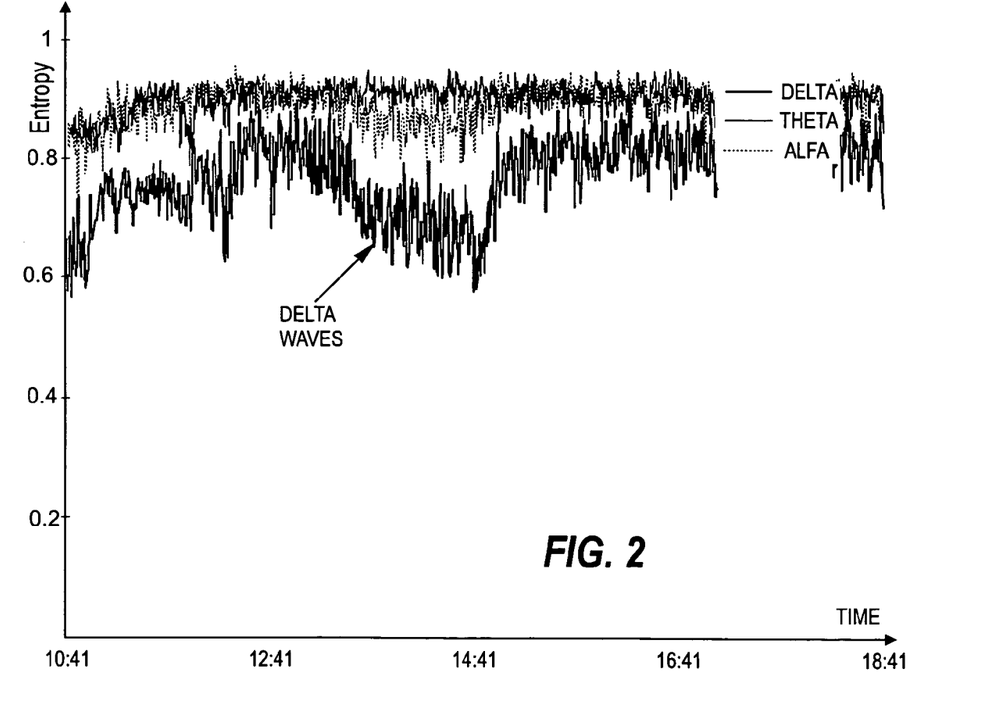
FIG. 2 illustrates the entropies of different EEG rhythms of a patient with healthy brain.

FIGS. 1 and 2 illustrate the entropies of the Delta, Theta and Alpha waves, measured during an eight hour period from two different patients. FIG. 1 shows the entropies measured from a sedated patient suspected to have encephalopathy (clinician's diagnosis), while FIG. 2 shows the entropies measured from a patient who is also sedated but has a healthy brain (clinician's diagnosis). As can be seen from the figures, the separator for these patients is the spectral entropy of the Delta waves. This is utilized in the present invention to sort out encephalopathic patients.

Figure 3:
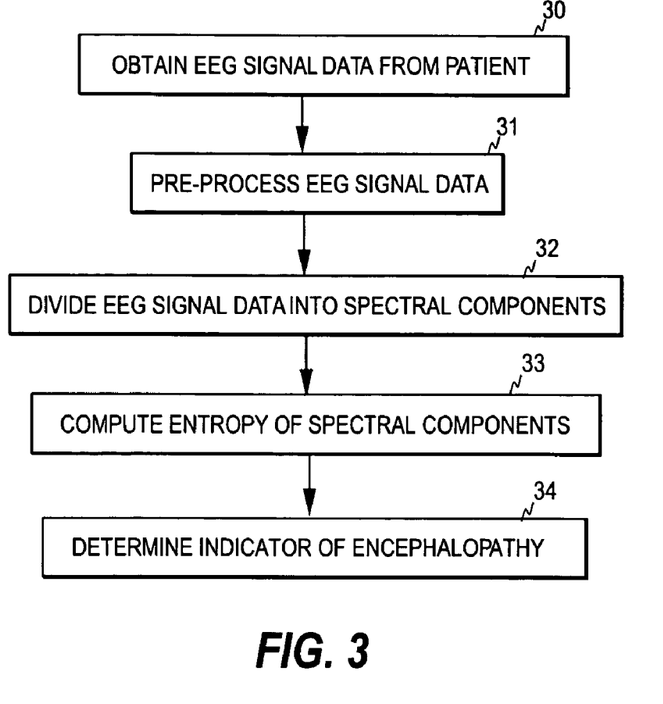
FIG. 3 is a flow diagram illustrating one embodiment of the method of the invention.

FIG. 3 is a flow diagram illustrating one embodiment of the invention utilizing the phenomenon shown in FIGS. 1 and 2. First, EEG signal data is obtained from the patient (step 30). The signal data may be collected in a conventional manner by converting the analog signals received from patient electrodes into digital format and storing the digital signals for further processing. The processing of the digitized signals typically uses sets of sequential signal samples representing finite blocks of time, commonly termed "epochs". Although the EEG signal data is stored prior to the being processed, encephalopathy may be monitored and detected almost in real-time.

Next, the EEG signal data is divided into a set of signal components, each signal component representing a certain frequency band of the EEG signal data (step 32). The EEG signal data is thus subjected to spectral decomposition. This may be carried out, for example, by a Fourier analysis. However, prior to the spectral decomposition, the signal data may be pre-processed for various purposes, such as for removing artifacts (step 31).

It is assumed in this example that the EEG signal data is divided into at least Delta and Theta components, i.e. that at least a component representing the Delta frequency band of the EEG signal data and a component representing the Theta frequency band of the EEG signal data are derived at step 32. When the signal components representing the different frequency bands have been obtained, a parameter indicative of the amount of disorder or complexity in the respective signal component is calculated based on each signal component (step 33). In this example, two parameters are thus obtained; a first parameter indicative of disorder/complexity in the signal component representing the Delta waves and a second parameter indicative of disorder/complexity in the signal component representing the Theta waves.

Currently, the calculation of entropy is deemed advantageous for calculating a parameter indicative of the amount of disorder or complexity in the spectral components of the EEG signal, due to the computational simplicity as compared to the other techniques available for computing such a parameter. However, any appropriate technique may be used to obtain the spectral components and the parameters indicative of the disorder or complexity in the components. For example, (time-domain) filtering may be used to divide the EEG signal data into time-domain components that represent the desired frequency bands, and the complexity of the components obtained may be calculated by the Lempel-Ziv algorithm. A more detailed discussion of the various mathematical techniques available for calculating parameters indicative of disorder or complexity can be found in the above-referred international patent application WO 02/32305. Since different mathematical techniques may be utilized, a parameter indicative of disorder refers in this context generally to a parameter, which may be indicative of the amount of disorder or complexity in the respective signal.

The parameters obtained are then used for determining an indicator of encephalopathy at step 34. In this example, the indicator is determined by calculating the difference of the two parameters obtained at step 33, i.e. the difference of the entropies of Theta and Delta waves. As can be seen from FIGS. 1 and 2, the difference between the entropies of the Theta and Delta waves is greater in case of a normal patient than in case of an encephalopathic patient. The indicator of encephalopathy is thus indicative of the presence of encephalopathy.

Generally, the indicator of encephalopathy is calculated based on a first parameter indicative of disorder in a signal component representing low frequencies, such as the Delta frequencies, of the EEG signal data, and based on a second parameter indicative of disorder in a second signal component representing a frequency band that includes higher frequencies than said low frequencies, such as the Theta frequency band. As discussed below, the frequency band of the second parameter may also include, in addition to the higher frequencies, the low frequencies, or part of them. Furthermore, the indicator of encephalopathy may be determined in various ways based on the two parameters.

The process then outputs a value for the indicator of encephalopathy. A clinician may use the value (which is updated at regular intervals) in analyzing the state of the patient. Alternatively, the the system of the invention may make a decision whether the patient is encephalopathic or not. For this, a threshold value may be determined in advance for the indicator of encephalopathy, and the value of the indicator may be compared with the threshold value to determine whether encephalopathy is detected or not. The threshold value may be defined by calculating the indicator of encephalopathy for a large group of encephalopathic and normal patients. As discussed below, the threshold may also be a line on plane defined by the indicator of encephalopathy and an additional discrimination parameter.

In the above embodiments, the indicator of encephalopathy was the only discrimination parameter used to discriminate between encephalopathic and normal patients. In another embodiment of the invention, an entropy value calculated from a wide frequency band stretching from low to higher frequencies and therefore indicating the overall level of sedation is used, in addition to the above-described subtracted entropy value, as a discrimination parameter for distinguishing an encephalopathic brain from a healthy brain. In the examples below, the additional discrimination parameter is an entropy value calculated from a frequency band of 1 to 13 Hz of the EEG signal, i.e. the entropy value of a frequency band approximately corresponding to the Delta, Theta and Alpha waves. Below, the indicator of encephalopathy, which is used in all embodiments of the invention, is termed the primary discrimination parameter, while the additional discrimination parameter is termed an auxiliary (discrimination) parameter.

Figure 4:
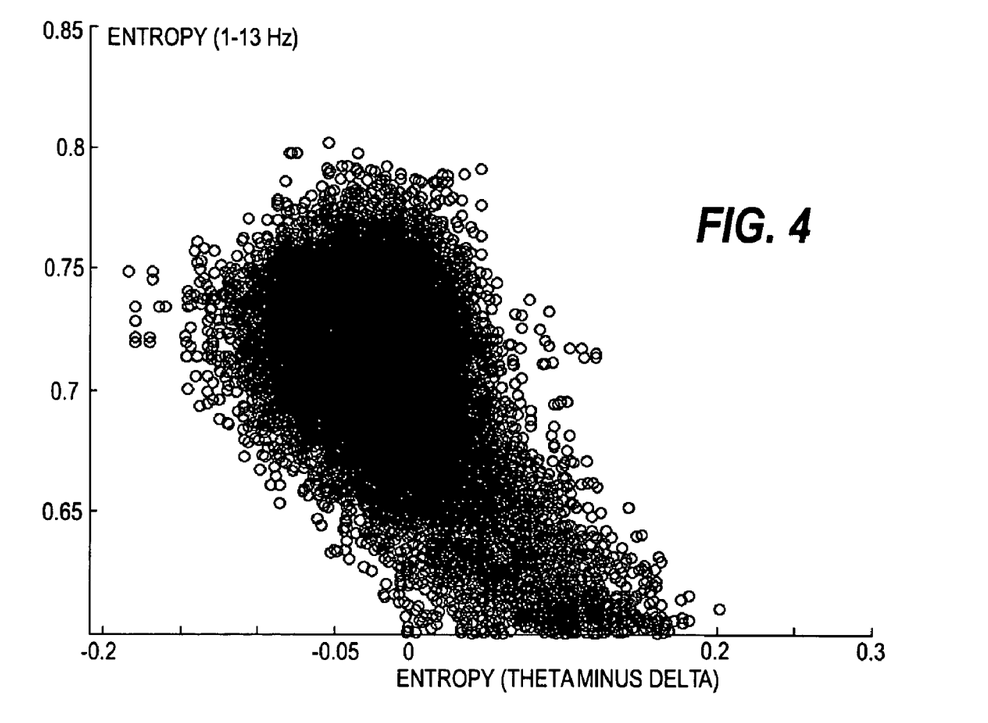
FIG. 4 is a scatterogram showing the data of FIG. 1.
Figure 5:
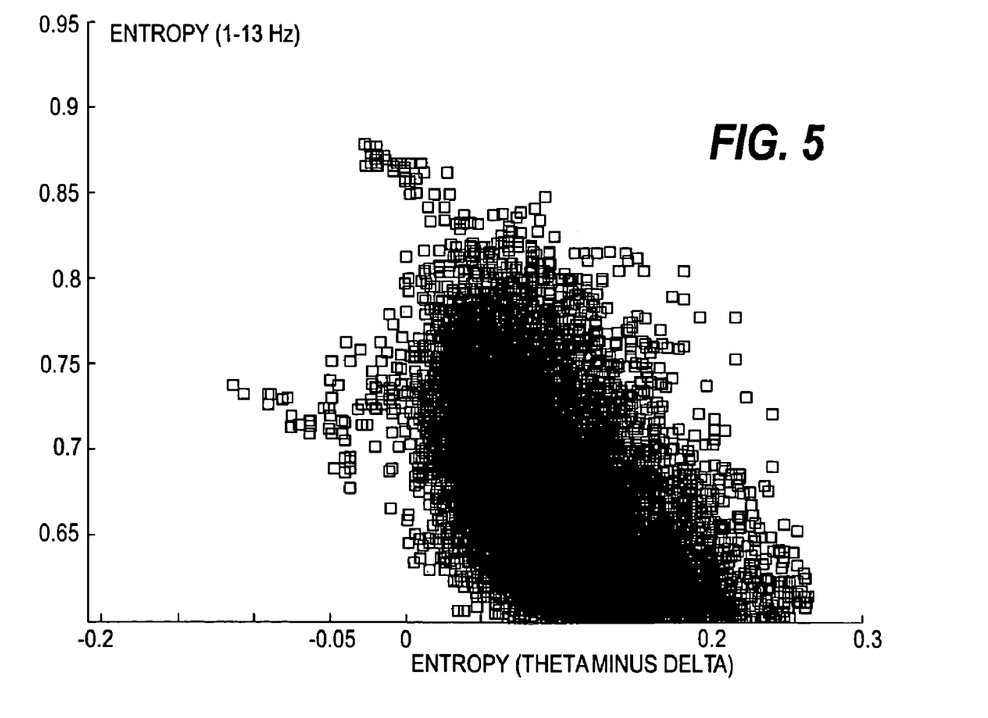
FIG. 5 is a scatterogram showing the data of FIG. 2.

FIGS. 4 and 5 are scatterograms created from the two above-mentioned parameters. FIG. 4 illustrates the data of FIG. 1, while FIG. 5 illustrates the data of FIG. 2. In both figures, the horizontal axis shows the difference of Theta and Delta entropies. As discussed in connection with FIGS. 1 and 2, if the Delta entropy is approximately the same as the Theta entropy (i.e. very high), the patient quite likely has encephalopathy. On the vertical axis, entropy calculated from a frequency band of 1 to 13 Hz shows the general response of Delta, Theta and Alpha waves to sedation and/or encephalopathy.

Low spectral entropy values indicate deep sedation. As can be seen from FIGS. 4 and 5, a patient who is in deep sedation (low entropy values on the vertical axis) may or may not have an encephalopathy. In terms of reliable measurement of the level of sedation and proper infusion of the sedatives, the low entropy values do not rise a problem, provided that the spectral entropy values react to the actual level of unconsciousness of the patient. If the entropy values are low, the patient may be unconscious due to encephalopathy or due to high amounts of medication. High spectral entropy values, in turn, usually indicate light sedation. However, as FIGS. 4 and 5 show a high value of spectral entropy may suggest two different things:

the patient has a healthy brain and he/she is only in light sedation or awake. In this case the entropy of the delta rhythm has variation in its (ir)regularity, as FIG. 2 shows.

the patient is unconscious with abnormally high entropy values and therefore likely with encephalopathy. The EEG signal in the Delta range is irregular, as FIG. 1 suggests.

The latter possibility may significantly increase the above-mentioned risk of over-sedation, as the high entropy values may advice the nursing staff to increase the infusion of sedatives. However, the present invention now provides a mechanism for identifying encephalopathic patients, thereby significantly reducing the above-mentioned risk of over-sedation.

As FIGS. 4 and 5 suggest, it is advantageous to use an entropy value calculated from a wider frequency band and indicative of the overall level of sedation as an additional parameter when a decision is made whether the patient is encephalopathic or not.

Figure 6:
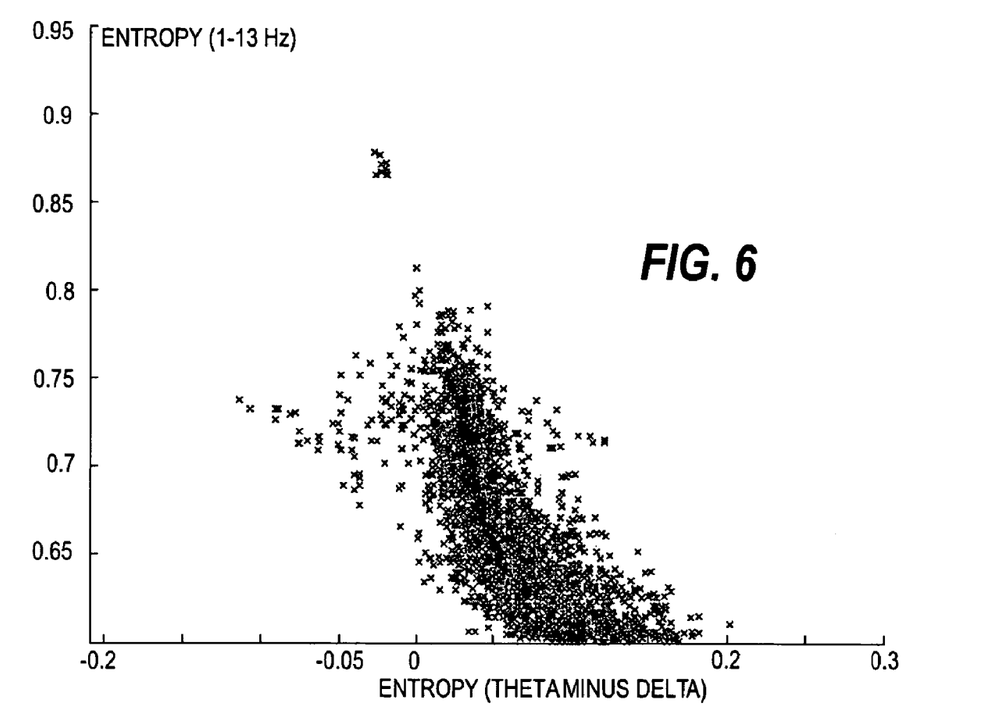
FIG. 6 is scatterogram showing misclassified samples when a linear classification method is applied to the data shown in FIGS. 4 and 5.

FIG. 6 shows the result of a linear classification method being applied to the data shown in FIGS. 4 and 5. As in FIGS. 4 and 5, the vertical axis represents the overall response to sedation, while the horizontal axis represents the primary discrimination parameter (here Theta entropy minus Delta entropy), i.e. the indicator of encephalopathy. The figure shows only the data points (samples) of FIGS. 4 and 5 that were misclassified with the linear classification method.

Figure 7:
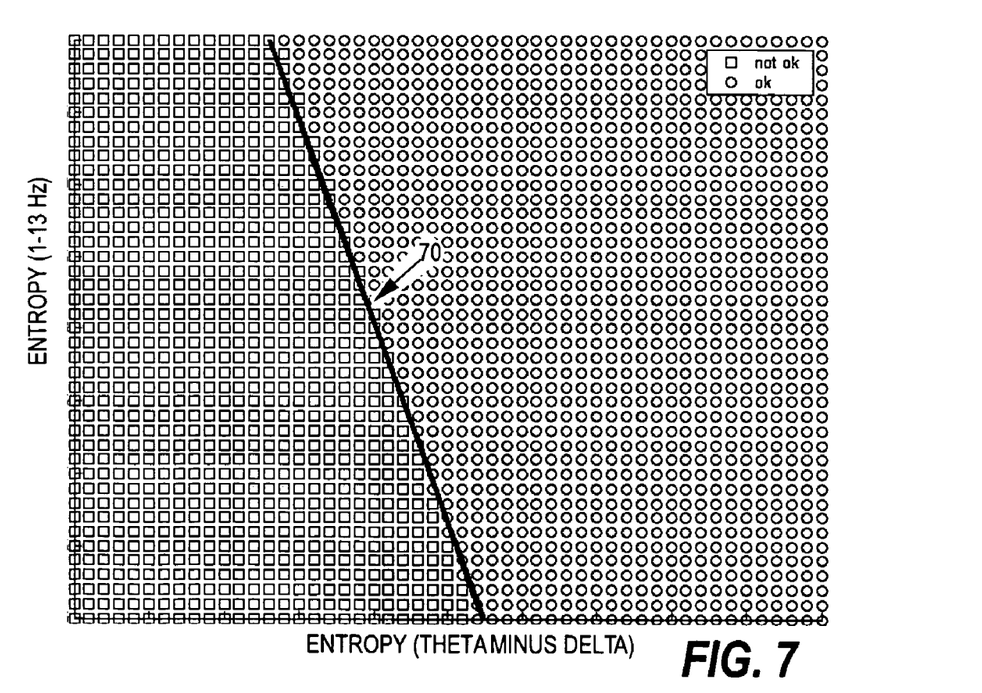
FIG. 7 illustrates the classification of the patients, when a threshold line is defined in advance for decision-making, the threshold line separating the "brain OK" and the "brain not OK" groups from each other.

By applying the concept of linear classification further, a threshold line between the "brain ok" (i.e. healthy brain) and the "brain not ok" (i.e. encephalopathic brain) groups may be obtained. FIG. 7 presents a plane, which has been separated into regions divided by a threshold line 70. In this example, the line is defined by the equation $y=kx+c$, where x presents the value of the primary discrimination parameter and y represents the auxiliary parameter. In this example, the values of the coefficients are $k=-2.7778$ and $c=0.8055$. With the linear classification method, the per cent of misclassifications in FIG. 6 is only 7.2, i.e. 7.2 per cent of the data points are on the "wrong" side of the threshold line.

The above-described parameter values calculated from the EEG signal data of a patient thus suggest whether the patient has an encephalopathy or not. A threshold line, such as line 70 in FIG. 7, may be defined based on parameters measured from a (large) patient group and the system of the invention may make the decision on the encephalopathy after having defined on which side of the threshold line the data point defined by the primary and auxiliary parameters is. The decision may be made at each data point, and the system may make a final decision on the presence of encephalopathy on a majority basis, for example, after having made a decision at a certain number of successive data points.

In practice, the decision may also be made based on a set of data points obtained during a certain measurement period, such as one hour, whereby the misclassification rate may be substantially decreased. Based on the data set obtained during the measurement period, various parameters may be determined for the decision-making. For example, the center of gravity of the data points may be calculated and the decision may be made based on the location of the center of gravity with respect to the threshold line. The decision may also be made based on the morphology (i.e. the form and/or size) of the data set obtained. Therefore, various parameters indicative of the form and/or size of the data set may be calculated for the decision-making, such as the width and/or height of the data set. The data set and the threshold line may also be presented graphically on a display device, enabling the nursing staff to make the decision on the presence of the encephalopathy based on the morphology of the data set and the threshold line.

In the above examples, the difference between the entropies of the Theta and Delta waves was used as the primary discrimination parameter and the entropy of the frequency band approximately corresponding to the Delta, Theta, and Alpha waves as the auxiliary parameter. However, these parameters may be determined in various ways. Generally, as encephalopathy induces disorder to the low frequency range of the EEG, a signal component representing the low frequencies of the EEG is to be derived from the EEG signal data obtained from the patient, and a first parameter indicative of disorder in the said signal component is to be computed in order to obtain a parameter that is specific to encephalopathy. The width of the frequency band based on which the first parameter is calculated may vary provided that the phenomenon shown in FIGS. 1 and 2 remains detectable in the first parameter. In one embodiment of the invention, the frequency band based on which the first parameter is calculated may extend from approximately 0.2 Hz up to approximately 10 Hz. However, the said frequency band is typically narrower. In another embodiment, the said frequency band may extend from approximately 0.5 Hz to approximately 7 Hz, while in embodiments that are currently preferred the upper limit of the said frequency band is closer to the border frequency of the Delta and Theta waves. These embodiments thus utilize a frequency band that extends from approximately 1 Hz to approximately 4 Hz for calculating the first parameter.

The value of the first parameter is then "compared" with the value of a second parameter indicative of disorder in an EEG signal component representing a predetermined frequency band including higher frequencies than said low frequencies. Instead of calculating the second parameter based on the Theta waves, the second parameter may also be computed based on the entire EEG signal, i.e. the, second parameter may be indicative of disorder in the whole EEG signal. The frequency band corresponding to the second parameter may thus be the whole EEG band or a portion of it, as long as it contains enough frequencies that are above the frequency band corresponding to the first parameter. In one embodiment of the invention, the frequency band based on which the second parameter is calculated may extend from approximately 4 Hz up to approximately 32 Hz. However, the upper limit of the said frequency band is typically lower. In another embodiment, the said frequency band may extend from approximately 4 Hz to approximately 13 Hz, while in embodiments that are currently preferred the upper limit of the said low frequency range is closer to the border frequency of the Theta and Alpha waves. In these embodiments, a frequency band extending from approximately 4 Hz to approximately 8 Hz is thus utilized for calculating the second parameter.

The determination of the indicator of encephalopathy may be performed in various ways based on the first and second parameters. In the above examples, the difference of the two was utilized, but the indicator of encephalopathy may also be calculated as any variable that indicates the relative magnitudes of the two parameters, such as their ratio.

In the embodiments that use the auxiliary parameter, such as the above-described entropy of the frequency band approximately corresponding to the Delta, Theta, and Alpha waves of the EEG signal data, the state of the patient is defined based on the values of the indicator of encephalopathy and the auxiliary parameter. The lower limit of the frequency band based on which the auxiliary parameter is determined is typically between 0 Hz and 4 Hz, while the upper limit is typically between 13 Hz and 32 Hz.

The method of the invention may also be used for making a prognosis on the cerebral state of the patient. The distance of the current data point from the threshold line may be tracked and a prognosis may be made based on the distance, the rate at which the distance changes, and/or the direction of the change, for example. The distance may also be calculated as a mean value of a certain number of data points. Thus, instead of tracking the current data point, a set of data points or parameters representing the set may also be tracked. For example, the center of gravity of the set and/or parameters describing the morphology of the set may be calculated at regular intervals, and the prognosis may be made based on the changes of the values of these parameters.

Figure 8:
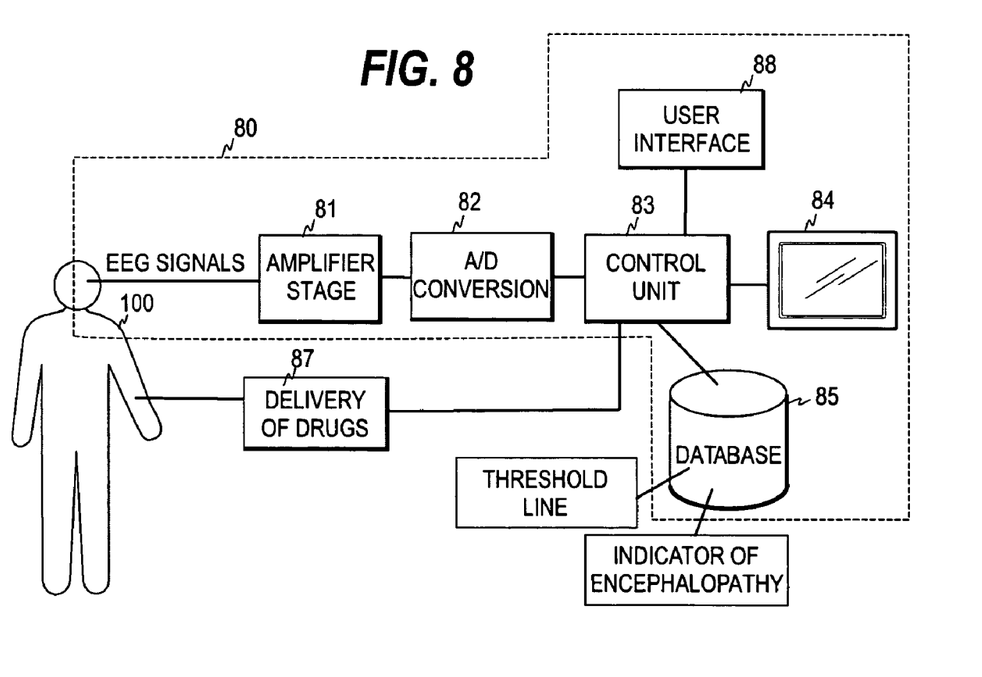
FIG. 8 illustrates one embodiment of the system according to the invention.

FIG. 8 illustrates one embodiment of the system according to the invention. The signals obtained from the EEG sensors attached to a patient 100 are supplied to an amplifier stage 81, which amplifies the signals before they are sampled and converted into digitized format in an A/D converter 82. The digitized signals are then supplied to a control unit 83 (including a microprocessor), which may then record the signals as an EEG time series.

The control unit is provided with a database or memory unit 85 holding the digitized EEG signal data obtained from the sensors. Using the data, the control unit may perform the above-described pre-processing phase for correcting the EEG signal data. The recording of the EEG signal data thus occurs in a conventional manner, i.e. the measurement device 80 including the above elements serves as a conventional EEG measurement device.

Additionally, the control unit is provided with algorithms for calculating the indicator of encephalopathy. The control unit thus derives a first signal component from the EEG signal data, the first signal component representing the low frequencies of the EEG signal data, and computes a first parameter indicative of disorder in the first signal component and a second parameter indicative of disorder in EEG signal data representing a predetermined first frequency band including higher frequencies than said low frequencies, such as the Theta frequency band. The control unit then determines an indicator of encephalopathy based on the first parameter and the second parameter. The control unit may further determine the auxiliary parameter and track how a data set measured during successive measuring periods moves on the plane defined by the indicator of encephalopathy and the auxiliary parameter. The decision-making, if utilized, may also take place in the control unit in the above-described manner.

Although one control unit (processor) may perform the calculations needed, the processing of the EEG signal data obtained may also be distributed among different processors (servers) within a network, such as a hospital LAN (local area network). For example, a conventional measurement device may record the EEG signal data and an external processor may be responsible for further calculations according to the invention.

The control unit may display the results on the screen of a monitor 84 connected to the control unit. This may be carried out in many ways using textual and/or graphical information. For example, graphical information according to FIG. 7 may be displayed, the location of the measured data points illustrating the state of the patient. The control unit may further supply the calculated results as input data to a device or system 87 delivering drugs to the patient. The results serve as controlling data controlling the treatment of the patient, i.e. the selection of the drugs to be used. For example, the results may advise the nursing staff or the device 87 to use a certain selection of drugs. An expert system residing in conjunction with the control unit or connected to the control unit may also determine a treatment recommendation based on the results calculated. The recommendation may include, for example, a suggestion concerning the type of medication and/or a suggestion about increase or decrease of the medication, such as a sedative, used currently.

The system further includes user interface means 88 through which the user may control the operation of the system.

The software enabling a conventional EEG measurement device 80 to detect a case of encephalopathy may also be delivered separately to the measurement device, for example on a data carrier, such as a CD or a memory card. In other words, a conventional EEG measurement device may be upgraded by a plug-in unit that includes software enabling the measurement device to detect a case of encephalopathy based on the EEG signal data it has obtained from the patient.

Although the invention was described above with reference to the examples shown in the appended drawings, it is obvious that the invention is not limited to these, but may be modified by those skilled in the art without departing from the scope and spirit of the invention. For example, the limits of the various frequency bands utilized may vary. However, the frequency band corresponding to the above-mentioned first parameter is to include a sufficient portion of the Delta frequencies so that the first parameter responds to encephalopathy and the indicator calculated is specific to encephalopathy. The number of auxiliary parameters may also be increased. If two auxiliary parameters are used, i.e. if the number of discrimination parameters is three, the threshold becomes a surface in the space defined by the three discrimination parameters. Furthermore, although the invention is primarily intended for sedated ICU patients, it may also be used in connection with non-sedated patients.

The invention claimed is:

1. A method for detecting a case of encephalopathy, the method comprising the steps of:
   obtaining EEG signal data from a patient;
   deriving a first signal component from the EEG signal data, wherein the first signal component represents a first frequency band of the EEG signal data, the first frequency band including low frequencies of the EEG signal data;
   computing a first parameter indicative of disorder in the first signal component and a second parameter indicative of disorder in signal data representing a second frequency band of the EEG signal data, the second frequency band including higher frequencies than the first frequency band; and
   determining an indicator of encephalopathy based on the first parameter and the second parameter, the indicator of encephalopathy being indicative of encephalopathy.

2. A method according to claim 1, wherein the first frequency band includes frequencies between approximately 0.2 Hz and approximately 10 Hz.

3. A method according to claim 1, wherein the first frequency band includes frequencies between approximately 1 Hz and approximately 4 Hz.

4. A method according to claim 1, wherein the determining step includes a step of calculating the difference of the second parameter and the first parameter.

5. A method according to claim 1, wherein the determining step includes a step of calculating the ratio of the first parameter and the second parameter.

6. A method according to claim 1, wherein the second frequency band includes frequencies between approximately 4 Hz and approximately 32 Hz.

7. A method according to claim 3, wherein the second frequency band includes frequencies between approximately 4 Hz and approximately 8 Hz.

8. A method according to claim 1, wherein the second frequency band includes substantially all frequencies of the EEG signal data obtained in the obtaining step.

9. A method according to claim 7, wherein the determining step includes a step of calculating the difference of the second parameter and the first parameter.

10. A method according to claim 1, further comprising a step of defining a threshold for detecting encephalopathy.

11. A method according to claim 10, further comprising a step of calculating a third parameter indicative of disorder in signal data representing a third frequency band of the EEG signal data.

12. A method according to claim 11, wherein the defining step includes defining the threshold, and wherein the threshold is represented by a line on a plane defined by two variables representing the indicator of encephalopathy and the third parameter.

13. A method according to claim 10, further comprising a step of making a decision on occurrence of encephalopathy based on the threshold and the indicator of encephalopathy.

14. A method according to claim 12, further comprising a step of making a decision on occurrence of encephalopathy based on the line, the indicator of encephalopathy, and the third parameter.

15. A method according to claim 11, wherein the third frequency band includes frequencies between approximately 1 Hz and an upper limit frequency of at least 13 Hz.

16. A method according to claim 11, wherein the third frequency band includes substantially all frequencies of the EEG signal data obtained in the obtaining step.

17. A method according to claim 14, wherein the step of making the decision includes a step of comparing the line with a data point defined by the indicator of encephalopathy and the third parameter.

18. A method according to claim 17, wherein the step of making the decision includes the sub-steps of:
deciding on occurrence of encephalopathy for a sequence of data points obtained during a certain measurement period, each data point representing the values of the indicator of encephalopathy and the third parameter at a particular instant during said measurement period; and
making a final decision on the occurrence of encephalopathy based on the deciding step.

19. A method according to claim 14, wherein the step of making the decision includes a step of comparing the line with a data set including a sequence of data points obtained during a certain measurement period, each data point representing the values of the indicator of encephalopathy and the third parameter at a particular instant during said measurement period.

20. A method according to claim 19, wherein the comparing step includes a step of calculating at least one descriptor indicative of the characteristics of the data set.

21. A method according to claim 20, wherein the calculating step includes calculating a center of gravity of the data set.

22. A method according to claim 21, wherein the comparing step includes calculating a distance between the threshold line and the center of gravity.

23. A method according to claim 12, further comprising a step of graphically presenting the line and a data set including a sequence of data points obtained during a certain measurement period, each data point representing the values of the indicator of encephalopathy and the third parameter at a particular instant during said measurement period.

24. A method according to claim 1, further comprising a step of supplying the indicator of encephalopathy as input data to a device controlling infusion of a sedative to the patient.

25. A method according to claim 1, wherein the determining step includes determining a time series of the indicator of encephalopathy.

26. A method according to claim 25, further comprising a step of making a prognosis on cerebral state of the patient.

27. An arrangement for detecting a case of encephalopathy, the arrangement comprising:
measurement means for obtaining EEG signal data from a patient;
first means for deriving a first signal component from the EEG signal data, wherein the first signal component represents a first frequency band of the EEG signal data, the first frequency band including low frequencies of the EEG signal data;
computing means for computing a first parameter indicative of disorder in the first signal component and a second parameter indicative of disorder in signal data representing a second frequency band of the EEG signal data, the second frequency band including higher frequencies than the first frequency band; and
determination means for determining an indicator of encephalopathy based on the first parameter and the second parameter, the indicator of encephalopathy being indicative of encephalopathy.

28. An arrangement according to claim 27, further comprising means for defining a threshold for detecting encephalopathy.

29. An arrangement according to claim 28, further comprising calculation means for calculating a third parameter indicative of disorder in signal data representing a third frequency band of the EEG signal data.

30. An arrangement according to claim 29, wherein the means for defining the threshold are configured to define a threshold represented by a threshold line for a plane defined by two variables representing the indicator of encephalopathy and the third parameter.

31. An arrangement according to claim 28, further comprising decision-making means for making a decision on occurrence of encephalopathy based on the threshold and at least one variable measured from the patient, the at least one variable including the indicator of encephalopathy.

32. An arrangement according to claim 30, further comprising decision-making means for making a decision on occurrence of encephalopathy based on the threshold line, the indicator of encephalopathy, and the third parameter.

33. An arrangement according to claim 30, further comprising display means for graphically presenting the threshold line and a data set including a sequence of data points obtained during a certain measurement period, each data point representing the values of the indicator of encephalopathy and the third parameter at a particular instant during said measurement period.

34. An arrangement according to claim 27, wherein the first frequency band includes frequencies between approximately 0.2 Hz and approximately 10 Hz.

35. An arrangement according to claim 27, wherein the first frequency band includes frequencies between approximately 1 Hz and approximately 4 Hz.

36. An arrangement according to claim 27, wherein the second frequency band includes frequencies between approximately 4 Hz and approximately 32 Hz.

37. An arrangement according to claim 35, wherein the second frequency band includes frequencies between approximately 4 Hz and approximately 8 Hz.

38. An arrangement according to claim 29, wherein the third frequency band includes frequencies between approximately 1 Hz and an upper limit frequency of at least 13 Hz.

39. A method for assisting a physician, the method comprising the steps of:
obtaining EEG signal data from a patient;
deriving a first signal component from the EEG signal data, wherein the first signal component represents a first frequency band of the EEG signal data, the first frequency band including low frequencies of the EEG signal data;
computing a first parameter indicative of disorder in the first signal component and a second parameter indicative of disorder in signal data representing a second frequency band of the EEG signal data, the second frequency band including higher frequencies than the first frequency band;
determining an indicator of encephalopathy based on the first parameter and the second parameter, the indicator of encephalopathy being indicative of encephalopathy; and
in response to the determining step, compiling a treatment recommendation for a physician.

40. A method according to claim 39, wherein the compiling step includes a recommendation of a type of medication to be used.

41. An arrangement for detecting a case of encephalopathy, the arrangement comprising:
- a measurement device configured to obtain EEG signal data from the patient;
- a first calculator configured to derive a first signal component from the EEG signal data, wherein the first signal component represents a first frequency band of the EEG signal data, the first frequency band including low frequencies of the EEG signal data;
- a second calculator configured to calculate a first parameter indicative of disorder in the first signal component and a second parameter indicative of disorder in signal data representing a second frequency band of the EEG signal data, the second frequency band including higher frequencies than the first frequency band; and
- a third calculator configured to determine an indicator of encephalopathy based on the first parameter and the second parameter, the indicator of encephalopathy being indicative of encephalopathy.

42. A computer program embodied on a computer-readable medium for detecting a case of encephalopathy, the computer program executing the steps of:
- deriving a first signal component from EEG signal data measured from a patient, wherein the first signal component represents a first frequency band of the EEG signal data, the first frequency band including low frequencies of the EEG signal data;
- computing a first parameter indicative of disorder in the first signal component and a second parameter indicative of disorder in signal data representing a second frequency band of the EEG signal data, the second frequency band including higher frequencies than the first frequency band; and
- determining an indicator of encephalopathy based on the first parameter and the second parameter, the indicator of encephalopathy being indicative of encephalopathy.

* * * * *